US00PP37333P2

(12) United States Plant Patent
Read

(10) Patent No.: US PP37,333 P2
(45) Date of Patent: Mar. 17, 2026

(54) ***LEUCANTHEMUM* PLANT NAMED 'Real Jewel'**

(50) Latin Name: ***Leucanthemum* x *superbum***
Varietal Denomination: Real Jewel

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 19/060,665

(22) Filed: Feb. 22, 2025

(51) Int. Cl.
*A01H 5/02* (2018.01)
*A01H 6/14* (2018.01)

(52) U.S. Cl.
USPC ..... Plt./285
CPC ..... *A01H 6/1408* (2018.05); *A01H 5/02* (2013.01)

(58) Field of Classification Search
USPC ..... Plt./285
See application file for complete search history.

*Primary Examiner* — Shubo Zhou
*Assistant Examiner* — Zachariah Allan Kay
(74) *Attorney, Agent, or Firm* — Weatherly IP Solutions, LLC; Karen P. Bechtold; James M. Weatherly

(57) ABSTRACT

A new cultivar of *Leucanthemum* plant named 'Real Jewel' that is distinguishable by its dense clumping basal-branching and upright plant habit and numerous long and narrow dark green leaves.

Figure 1:
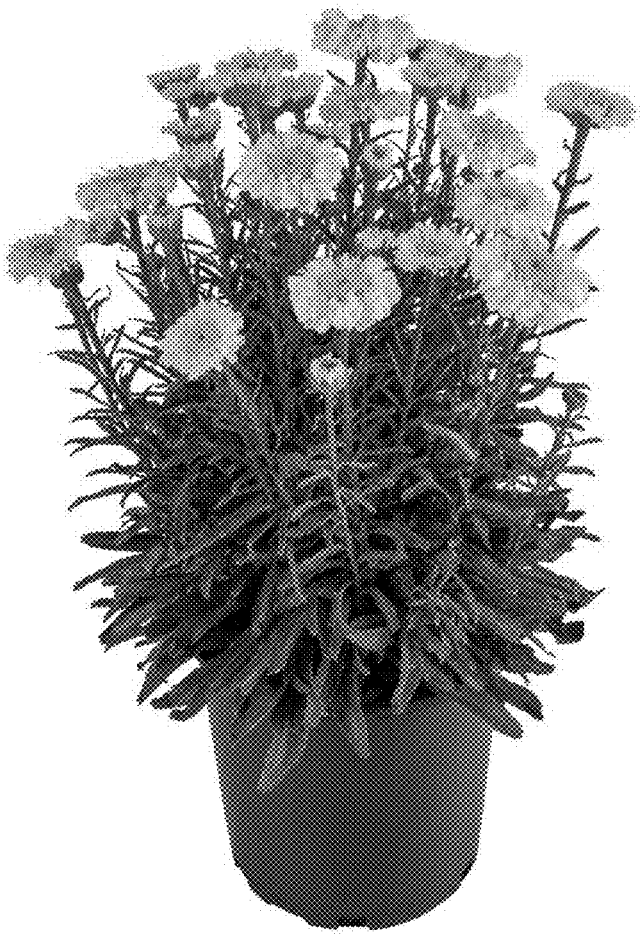

A fully expanded inflorescence of 'Real Jewel' is shallow cylindrical in shape and consists of approximately 60 ray florets borne in three concentric whorls surrounding approximately 400 yellow disc florets massed in a receptacle. Flowering of 'Real Jewel' commences in April and continues until October. The ray florets of 'Real Jewel' are lightly quilled towards the receptacle and then free and held slightly above the horizontal as they emerge from the perimeter of the disc and expand.

'Real Jewel' is hardy in USDA Zone 5 to (−20° F. or −28° C.). The foliage of 'Real Jewel' does not wilt in dry conditions.

2 Drawing Sheets

Genus and species: *Leucanthemum* x *superbum*.
Variety denomination: 'Real Jewel'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Jewel'.

*Leucanthemum* is a genus within the family Asteraceae in which the commonly referred to "flower" is botanically the inflorescence which is comprised of outer showy ray florets surrounding smaller disc florets.

'Real Jewel' arose and was selected from an ongoing breeding program which is conducted by the inventor at the inventor's nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Jewel' is a seedling selection that resulted from the controlled pollination in 2011 of a single plant of the inventor's proprietary *Leucanthemum* seedling code L1203-1 (unreleased and unpatented) as the female parent, using pollen from a single plant of the inventor's proprietary *Leucanthemum* seedling code L1128-5 (unreleased and unpatented) as the male parent. The inventor selected 'Real Jewel' in 2014 for its combination of tight clumping basal branching and upright habit, small narrow foliage and inflorescences which vary from cream to yellow in color of which many of the inflorescences are bright and deep yellow in color. The inflorescences of 'Real Jewel' are held on vertically erect stiff and rigid flower stems.

'Real Jewel' was first asexually propagated by the inventor in West Sussex, United Kingdom in 2018 using the method of vegetative division and subsequently by basal shoot cuttings. Since that time under careful observation 'Real Jewel' has been determined uniform, stable and true to type in subsequent generations of asexual propagation.

SUMMARY

The following traits have been repeatedly observed and represent the distinguishing characteristics of 'Real Jewel'. In combination, these traits set 'Real Jewel' apart from all other existing varieties of *Leucanthemum* known to the inventor. 'Real Jewel' has not been tested under all possible conditions and phenotypic differences may be observed with variations in environmental, climatic, and cultural conditions, however, without any variance in genotype.

1. 'Real Jewel' exhibits tight clumping basal-branching and an upright plant habit.
2. A mature plant of 'Real Jewel' growing in a 2-gallon container, or planted in the ground, is 20 cm to 22 cm in height to the top of the foliage mound, and 40 cm in diameter across the foliage mound. A mature fully flowering plant of 'Real Jewel' is 32 cm in height from soil level to the uppermost flowers.

3. The leaves of 'Real Jewel' are uniformly long and narrow.
4. A fully expanded inflorescence of 'Real Jewel' is shallow cylindrical in shape.
5. A fully expanded inflorescence of 'Real Jewel' consists of approximately 60 ray florets borne in three concentric whorls and approximately 400 yellow disc florets.
6. The ray florets of 'Real Jewel' are lightly quilled towards the receptacle and then free as they emerge from and around the perimeter of the disc.
7. Initially, the ray florets of 'Real Jewel' are held vertically and are deeper yellow in color than when further developed.
8. The yellow-colored ray florets of fully developed inflorescences of 'REAL JEWEL' are held at 30° to 35° above the horizontal. As the inflorescence ages and fades to cream in color, the ray florets of 'REAL JEWEL' are held between horizontal and 15° above the horizontal.
9. Flowering of 'Real Jewel' commences in April and continues until October.
10. 'Real Jewel' is hardy in USDA Zone 5 (−20° F. or −28° C.). The foliage of 'Real Jewel' does not wilt in dry conditions.

BRIEF DESCRIPTION OF THE PHOTOGRAPHS

The accompanying color photographs illustrate the overall appearance of 'Real Jewel' showing the color of foliage and inflorescence as true as is reasonably possible to obtain in color reproductions of this type. The illustrated plant was pinched at approximately 5 cm above soil and grown-on without any pruning or use of chemical growth regulators. The colors in the photographs may differ from color values cited in the detailed botanical description, which accurately describes the actual color of 'Real Jewel'.

FIG. 1 illustrates a four-year old plant of 'Real Jewel' which has been grown outdoors in a 2-gallon container in full sun in Santa Barbara, California. The photograph was taken in April 2022, and the illustrated plant is approaching full flower.

Figure 2:
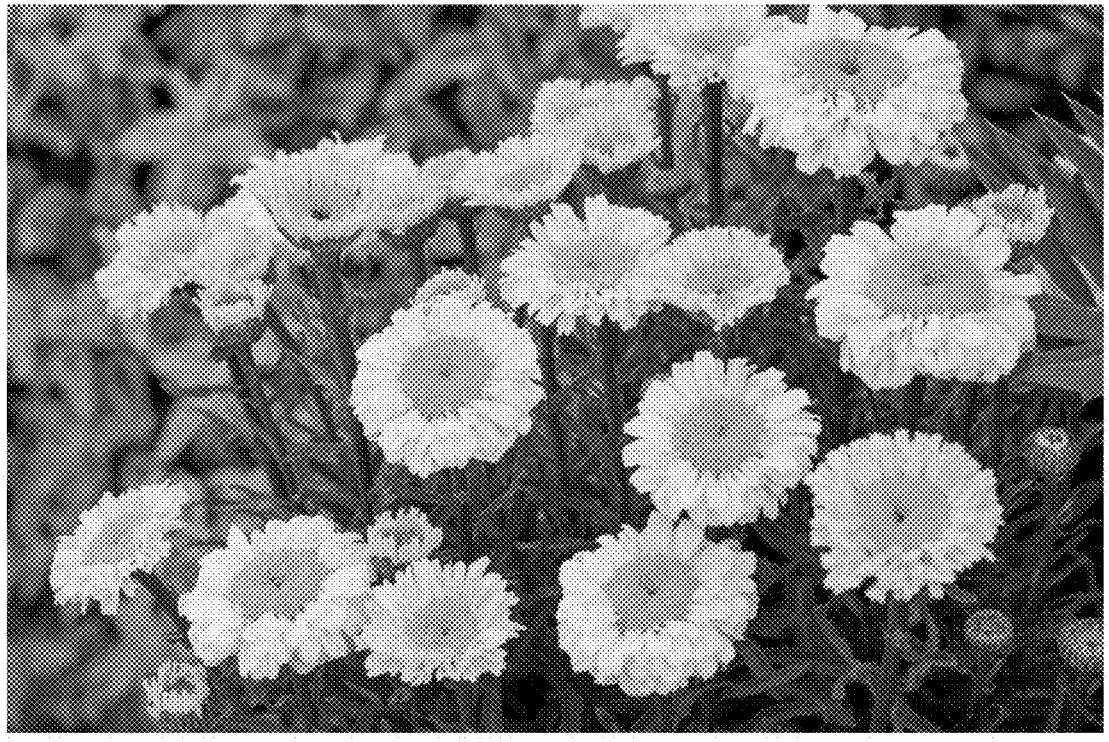

FIG. 2 presents a close-up view of fully developed inflorescences of a four year-old 'Real Jewel' plant, including inflorescences which are newly opened and mid-yellow in color and older inflorescences whose ray flowers have faded to cream-yellow, then cream and eventually to white in color.

BOTANICAL DESCRIPTION OF THE PLANT

The following is a detailed botanical description of the new cultivar 'Real Jewel'. Observations, measurements, values and comparisons were collected in Santa Barbara, California during April 2022, from a 4-year-old plant growing outdoors in 2-gallon container. The observed plant had been pinched at 5 cm above soil and grown-on without any pruning or use of chemical growth regulators. Color determinations are made in accordance with the 2007 edition of The Royal Horticultural Society Colour Chart from London, England, except where general color terms of ordinary dictionary significance are used.

Botanical classification:

*Family*.—Asteraceae (formerly Compositae).
*Genus*.—*Leucanthemum*.
*Species*.—X *superbum*.
*Denomination*.—'Real Jewel'.
*Common name*.—Shasta daisy.
*Habit*.—Prolific clumping basal-branching upright growth habit.
*Commercial category*.—Perennial.
*Use*.—For garden and landscape.
*Suggested commercial container size*.—4-inch, 1-gallon, and 2-gallon containers. Larger containers may be used for producing specimen or display plants.
*Parentage*.—*Leucanthemum* x *superbum* 'Real Jewel' is a seedling selection resulting from the controlled cross-pollination of the following parents — Male parent: inventor's proprietary *Leucanthemum* seedling code L1128-5. Female parent: inventor's proprietary *Leucanthemum* seedling code L1203-1.
*Propagation method*.—Basal shoot cuttings, division and tissue culture.
*Rooting system*.—Fine and fibrous.
*Vigor*.—Prolific production of basal stems and lateral branches.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—10 to 12 weeks are required from planting a rooted cutting or young plant to produce a flowering plant in a 1-gallon container. 12 to 14 weeks are required to produce a full plant in a 2-gallon container.
*Plant dimensions* (*one year*).—20 cm in height and 35 cm in width.
*Plant dimensions* (*end of season, plant fully flowering*).—32 cm in height from soil level to uppermost inflorescence, 35 cm in width.
*Cultural requirements*.—Grow in full sun and rich, moist moderately fertile well-draining soil.
*Pest or disease resistance and susceptibility*.—No specific disease or pest resistance or susceptibility has been observed or is known to the inventor.
*Drought tolerance*.—Moderate as the tightly arranged narrow foliage is less prone to wilting.
*Hardiness*.—USDA Zone 5.

Stems, branches: All basal stems originate from underground and bear secondary branches above ground. All stems and branches bear terminal inflorescences.

*Quantity*.—Approximately 75 basal stems and secondary branches.
*Stem length*.—20 cm to 32 cm.
*Stem diameter*.—3 mm to 4 mm, becoming wider 4 mm to 5 mm beneath inflorescence.
*Stem shape*.—Terete with longitudinal parallel ridges approximately 0.5 mm to 1 mm apart.
*Stem surface*.—Glabrous.
*Stem color* (*new stem shoots*).—RHS 138C.
*Stem color* (*fully grown stems*).—RHS 138A.
*Stem strength*.—Stiff and rigid.

Foliage:

*Type* (*division*).—Simple.
*Arrangement*.—Alternate.
*Attachment*.—Sessile.
*Internode*.—Ranges between 3 mm and 16 mm.
*Leaf dimensions* (*fully developed*).—17 cm in length, 15 mm in width.
*Apex*.—Acute.
*Base*.—Truncate, clasping.

*Leaf shape*.—Lanceolate becoming broadly elliptical towards apex.

*Margin*.—Serrate, 9 to 14 teeth spaced at 3 mm to 5 mm intervals, depth 0.5 mm.

*Leaf color* (*elliptical section towards apex*).—Adaxial surface RHS 137A, abaxial surface RHS 137D.

*Leaf color* (*narrow lanceolate section towards base*).—RHS 157B (both surfaces).

*Leaf venation*.—Pinnate, adaxial midrib depressed, abaxial midrib raised, approximately 0.5 mm above abaxial leaf surface.

*Vein color* (*both surfaces*).—As leaf except adaxial midrib ranges between RHS 138D and RHS 138B.

*Leaf surface* (*both surfaces*).—Glabrous, semi-glossy.

Inflorescence:

*Inflorescence type*.—Capitulum, consisting of ray florets and disc florets.

*Inflorescence shape*.—Initially shallow cylindrical becoming taller cylindrical, 15 mm in height from lowest ray floret to uppermost ray floret.

*Inflorescence quantity per plant*.—Approximately 25 to 30 including 6 to 8 newly opened buds.

*Inflorescence diameter* (*maximum*).—50 mm.

*Inflorescence height*.—8 mm when ray florets first visible, 15 mm when ray florets are fully developed.

*Inflorescence aspect*.—Upright.

*Inflorescence colors* (*when fully developed*).—Ray florets (newly emerged and for first 5-7 days): Individual ray florets colors range in color from RHS 6A to RHS 9A. Ray florets (fully expanded, for 8-15 days): Color RHS 6D. Ray florets after 15 days until senescence: Colors fade with age from RHS 6D initially to pale yellow RHS 4D and finally to pale yellow-white RHS 155A. Central disc: RHS 153D.

*Fragrance*.—Slightly musty.

*Blooming season*.—April to October.

*Lastingness of inflorescence* (*range*).—12 to 15 days on the plant, ray florets are persistent.

Bud:

*Bud dimensions* (*prior to first showing of ray florets*).—9 mm in height and 12 mm in diameter.

*Bud shape*.—Oblate (flattened top and base) spheroid.

*Bud color* (*adaxial surfaces of the clasping sepals*).—RHS 148C with prominent sepal margins RHS N186.

Ray florets:

*Shape*.—Lanceolate and lightly quilled at attachment to peduncle.

*Ray floret color* (*both surfaces*).—Predominantly RHS 6A. Occasionally ray florets much lighter yellow, RHS 2D.

*Ray floret color* (*apex*).—Ranges between RHS 2D and vary pale yellow white RHS 155A.

*Quantity per inflorescence*.—Average 60 ray florets per inflorescence.

Ray floret petals (first emergence):

*Arrangement, aspect*.—Whorled in three closely adjacent whorls. Petals initially held vertically or approximately 20° to 30° away from the vertical.

*Corolla tube*.—3 mm in length, 1.0 to 1.5 mm in diameter.

*Corolla tube color* (*both surfaces*).—RHS 144D.

*Surface* (*both*).—Glabrous, glossy.

*Ray floret petal shape*.—Narrow lanceolate, occasionally broad below apex.

*Ray floret dimensions* (*initially*).—9 mm to 17 mm in length, 1.0 to 1.2 mm in width.

*First emerging ray floret color* (*both surfaces*).—Predominantly RHS 6A and occasionally much lighter yellow RHS 2D and at petal apex.

Ray floret petals (petals fully developed):

*Ray floret arrangement*.—Three-whorled, consisting of 60 smaller ray florets initially held vertically and arising from the perimeter of the bud and disc. These same 60 ray florets expand to be held eventually at approximately 10° to 15° above the horizontal.

*Corolla tube*.—3 mm in length, 1.0 to 1.5 mm in diameter.

*Corolla tube color* (*both surfaces*).—RHS 144D.

*Surface* (*both*).—Glabrous, glossy.

*Petal shape*.—Narrow lanceolate, occasionally broadening to 3 mm in width below apex.

*Ray floret petal dimensions* (*fully developed*).—14 mm to 17 mm in length, 1.0 to 1.2 mm in width, occasionally up to 3.0 mm in width below apex.

Disc, disc florets:

*Disc diameter*.—2.5 cm to 3.0 cm.

*Disc floret quantity*.—Approximately 400 per inflorescence, massed at center of receptacle.

*Receptacle*.—Shape: Convex. Dimensions: 3 cm in diameter, 4 mm in height in center.

*Disc floret color*.—RHS 153D.

*Disc floret shape*.—Tubular, consisting of five fused petals and free and flared petal lobes.

*Disc floret tube dimensions*.—5 mm to 6 mm in length, 1 mm in diameter.

*Disc floret lobe dimensions*.—2 mm in length, 1 mm in diameter.

*Disc floret corolla tube* (*visible when disc floret pulled from receptacle*).—Color RHS 17A.

*Disc floret petal apex*.—Acute.

*Disc floret petal base*.—Truncate.

Disc floret peduncle.—3 mm to 4 mm in length, 0.75 mm in diameter, smooth, color RHS 144C to RHS 144D.

Involucral bracts:

*Arrangement*.—Present below buds and becoming larger below fully expanded inflorescences.

*Quantity* (*average*).—4 to 6 bracts (2 to 3 opposite pairs per inflorescence or bud).

*Bract shape*.—Short lanceolate, irregular, occasionally twisted and recurved.

*Dimensions* (*bud bracts*).—4 mm to 6 mm in length, 3 mm in width.

*Dimensions* (*inflorescence bracts*).—5 mm to 8 mm in length, 4 mm in width.

*Texture*.—Stiff, matte.

*Bract color* (*adaxial surface*).—RHS 137A.

*Bract color* (*abaxial surface*).—RHS 137D.

*Bract apex*.—Ciliate and rounded (bud bracts), Smooth, acute (inflorescence bracts).

Bud bract apex cilia.—1 mm to 2 mm in length, fine, color RHS 200C.

*Bract base*.—Truncate.

*Bract surface* (*both surfaces*).—Glabrous except ciliate apex.

*Bract margin*.—Serrate, teeth appear as short pale green spines, length 1 mm and 1 mm apart.

Reproductive organs:

*Ray florets*.—Androecium (stamens, anthers, filaments, pollen): Absent. Pistil: 1.2 mm in length, hair-like, diameter less than 0.2 mm. Color RHS 162C. Stigma: Tripartite, 1.5 mm in length, hair-like, diameter less than 0.2 mm, color RHS 162C. Ovary: Not observed.

*Disc florets*.—Stamens: 5, fine hair-like, reflexed at apex, length 3 mm, diameter less than 0.5 mm, color RHS 17A. Anthers: Not visible. Pollen: Slight amount, color RHS 23A. Ovary: Not observed.

Seed: None observed to date.

COMPARISON WITH PARENTAL LINES

In comparison with both of its parents, plants of 'Real Jewel' are shorter and more compact florets, with a dense canopy of small narrow leaves. The parent selections bear cream to light yellow ray florets whereas the ray florets of 'Real Jewel' are bright deep yellow in color.

COMPARISON WITH KNOWN VARIETY

The commercial variety of *Leucanthemum* which the inventor considers to most closely resemble 'Real Jewel' is the inventor's variety of *Leucanthemum* Plant Named 'Real Cream' (U.S. Plant Pat. No. 35,400). The inflorescences of 'Real Jewel' are flat cylindrical in shape whereas the inflorescences of 'Real Cream' are flat. 'Real Jewel' bears many more (typically 60, closely packed and overlapping) ray florets borne in three whorls whereas 'Real Cream' which bears approximately 30 non-overlapping ray florets in one whorl only.

I claim:

1. A new and distinct cultivar of *Leucanthemum* plant named 'Real Jewel' as described and illustrated herein.

* * * * *